(12) United States Patent
Hessler et al.

(10) Patent No.: US 12,324,745 B2
(45) Date of Patent: Jun. 10, 2025

(54) ARTICULATING EXPANDABLE INTERBODY FUSIONS DEVICES

(71) Applicant: GLOBUS MEDICAL, INC., Audubon, PA (US)

(72) Inventors: Ty Hessler, Phoenixville, PA (US); Chad Glerum, Pennsburg, PA (US); Mark Weiman, Downingtown, PA (US); Albert Hill, Richboro, PA (US); Myles Sullivan, Philadelphia, PA (US)

(73) Assignee: Globus Medical Inc., Exton, PA (US)

( * ) Notice: Subject to any disclaimer, the term of this patent is extended or adjusted under 35 U.S.C. 154(b) by 480 days.

(21) Appl. No.: 17/502,522

(22) Filed: Oct. 15, 2021

(65) Prior Publication Data

US 2022/0031471 A1 Feb. 3, 2022

Related U.S. Application Data

(63) Continuation of application No. 16/750,591, filed on Jan. 23, 2020, now Pat. No. 11,154,405.

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30149* (2013.01); *A61F 2002/4485* (2013.01)

(58) Field of Classification Search
CPC ...... A61F 2/4425; A61F 2/4455; A61F 2/447; A61F 2/44; A61F 2/4611; A61B 2002/4415; A61B 2002/448–4485; A61B 2002/30136–30158; A61B 2002/30535–30545; A61B 2002/30556
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Eduardo C Robert
*Assistant Examiner* — Michelle C Green (57) ABSTRACT

Articulating expandable fusion devices, systems, instruments, and methods thereof. The articulating expandable fusion implant having a plurality of links is capable of being deployed and articulated inside an intervertebral disc space link by link. After the links are articulated into a polygonal shape, the links may be expanded outwardly into an expanded configuration. Instruments may be provided to articulate and expand the implant.

20 Claims, 7 Drawing Sheets

(56) References Cited

U.S. PATENT DOCUMENTS

| | | |
|---|---|---|
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,387,130 B1 * | 5/2002 | Stone .................. A61F 2/4611 623/17.16 |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 10,631,971 B2 * | 4/2020 | Kalfon .................. A61F 5/0036 |
| 11,154,405 B2 * | 10/2021 | Hessler .................. A61F 2/4611 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0041258 A1 * | 2/2006 | Galea .................. A61F 2/4455 606/279 |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221687 A1 * | 9/2008 | Viker .................. A61F 2/4455 623/17.16 |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0312743 A1 * | 12/2008 | Vila .................. A61F 2/4611 623/17.11 |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0240335 A1 * | 9/2009 | Arcenio .................. A61B 17/7094 623/17.11 |

(56) References Cited

U.S. PATENT DOCUMENTS

| | | |
|---|---|---|
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0110239 A1* | 5/2013 | Siegal ............... A61F 2/46 623/17.16 |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0058513 A1* | 2/2014 | Gahman ............ A61F 2/442 623/17.16 |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2014/0277481 A1* | 9/2014 | Lee .................. A61F 2/4601 623/17.16 |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0257894 A1* | 9/2015 | Levy .................. A61F 2/442 623/17.15 |
| 2015/0289988 A1 | 10/2015 | Ashley et al. |
| 2015/0374508 A1 | 12/2015 | Sandul |
| 2016/0166396 A1 | 6/2016 | McClintock |
| 2016/0199195 A1* | 7/2016 | Hauck ............... A61F 2/4455 29/433 |
| 2016/0324654 A1 | 11/2016 | Loebl et al. |
| 2017/0020570 A1* | 1/2017 | Petersheim ........ A61B 17/7001 |
| 2017/0100258 A1 | 4/2017 | Jimenez et al. |
| 2017/0119543 A1 | 5/2017 | Dietzel et al. |
| 2019/0008654 A1* | 1/2019 | Thommen ......... A61F 2/4611 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| JP | 2010518987 A | 6/2010 |
| JP | 2015512328 A | 5/2015 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2013006669 A2 | 4/2013 |
| WO | 2015009793 A1 | 1/2015 |

* cited by examiner

ARTICULATING EXPANDABLE INTERBODY FUSIONS DEVICES

CROSS-REFERENCE TO RELATED APPLICATIONS

The present application is a continuation of U.S. patent application Ser. No. 16/750,591, filed Jan. 23, 2020, which is incorporated herein in its entirety.

FIELD OF THE INVENTION

The present disclosure relates to surgical devices, and more particularly, to articulating expandable fusion devices capable of being deployed inside an intervertebral disc space and then expanded to maintain disc spacing, restore spinal stability, and/or facilitate an intervertebral fusion.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing conventional fusion devices often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In accordance with the application, devices, systems, methods, and instruments are provided. In particular, an articulating expandable fusion device is provided, which is capable of being deployed inside an intervertebral disc space to maintain normal disc spacing, restore spinal stability, and/or facilitate an intervertebral fusion. The device may be installed in an open, semi-open, or minimally invasive surgical procedure. The articulating expandable fusion device may be capable of being placed into the disc space down a guide tube, for example, articulated into a polygonal shape, and then expanded into an expanded configuration.

According to one embodiment, an expandable implant includes a first link, a second link pivotally connected to the first link, and a third link pivotally connected to the second link. Each of the links comprises an upper body having one or more ramped surfaces, a lower body having one or more ramped surfaces, and a middle body positioned between the upper and lower bodies and having one or more ramped surfaces. Translation of the middle bodies causes the one or more ramped surfaces of the middle bodies to slide against the one or more ramped surfaces of the upper and lower bodies, thereby resulting in expansion of the expandable implant.

The links may be configured to articulate into a polygonal shape, such as a triangle, a square, a pentagon, a hexagon, etc. The one or more ramped surfaces of the upper and lower bodies, respectively, may define male ramps, and the one or more ramped surfaces of the middle bodies may define female ramps or vice versa. One or more of the ramps may mate as dovetail slide ramps, T-slots or similar mechanisms.

The links may be connected by one or more retaining rings configured for holding one or more pivot pins. For example, each of the upper bodies may include first and second upper retaining rings, and each of the lower bodies may include first and second lower retaining rings. The second upper retaining ring of the first link may connect to the first upper retaining ring of the second link with a first pivot pin. The second lower retaining ring of the first link may connect to the first lower retaining ring of the second link with a second pivot pin. The second upper retaining ring of the second link may connect to the first upper retaining ring of the third link with a third pivot pin. The second lower retaining ring of the second link may connect to the first lower retaining ring of the third link with a fourth pivot pin. Additional links, retaining rings, and pivot pins may be used if needed.

According to another embodiment, an implantable device includes a plurality of links configured to articulate with respect to one another. Each of the links may include an upper body, a lower body, and a middle body positioned between the upper and lower bodies. The upper body may include an upper bone contacting surface configured to engage bone and a lower surface having a first ramp. The lower body may include an upper surface having a second ramp and a lower bone contacting surface configured to engage bone. The middle body may include an upper surface having a third ramp and a lower surface having a fourth ramp. The first ramp of the upper body may mate with the third ramp of the middle body and the second ramp of the lower body may mate with the fourth ramp of the middle body. Movement of the middle body may cause the third ramp to slide against the first ramp and the fourth ramp to slide against the second ramp, thereby resulting in an expansion of the upper and lower bodies of the plurality of links.

According to another embodiment, an implantable system includes an articulatable and expandable implant and an inserter instrument. The articulatable and expandable implant may include a plurality of links pivotally connected to one another. Each of the links may include an upper body having one or more ramped surfaces, a lower body having one or more ramped surfaces, and a middle body positioned between the upper and lower bodies and having one or more ramped surfaces configured to mate with the one or more ramped surfaces of the upper and lower bodies, respectively.

The inserter instrument may include a guide tube, an insertion driver, and a cable. The guide tube may be configured for deploying the plurality of links into a disc space. The insertion driver and cable may be configured for articulating the plurality of links into a polygon. The cable may be further configured for applying an inward force to the middle bodies of the links to translate the middle bodies towards a center of the polygon, thereby causing linear expansion of the upper and lower bodies. The middle bodies may include a plurality of openings configured for receiving the cable therein. The insertion driver may apply a push force to the plurality of links and the cable may apply a pull force to the plurality of links to articulate the plurality of links. The cable may be configured to shorten in circumferential distance to provide the inward force against the middle bodies and translate the middle bodies inwards toward the center of the polygon, thereby expanding the implant.

According to yet another embodiment, methods of installing and articulating the expandable implant are provided. A disc space of a patient may be accessed and prepared. The implant may be positioned within the disc space via an inserter instrument, for example, link by link. The links may be articulated by the inserter instrument into a polygon, such as a pentagon. The links may be expanded by moving the middle bodies of the respective links, for example, by translating the middle bodies inward toward the center of the polygon. The inserter instrument may be withdrawn from the patient's body, thereby leaving the implant in the articulated and expanded position.

Also provided are kits including articulating expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Interbody devices have been used to provide support and stability in the anterior column of the spinal vertebrae when treating a variety of spinal conditions, such as degenerative disc disease and spinal stenosis with spondylolisthesis. Clinical treatment of spinal pathologies with anterior vertebral body interbody devices relies on precise placement of the interbody implant to restore normal anterior column alignment. Iatrogenic pathologies may result from the surgical access window to the disc space, failure to precisely place the interbody on hard cortical bone often found on the apophyseal ring of the vertebral body, and/or failure to precisely control and restore normal anatomical spinal alignment.

There currently exists a need to provide precise placement of interbody support that increases interbody contact with hard cortical bone and/or provides precise control of anterior column alignment while reducing the profile of the access window to the disc space. Accordingly, embodiments of the present application are generally directed to devices, systems, instruments, and methods for installing, articulating and expanding the interbody implant. The terms implant, interbody, interbody implant, fusion device, spacer, and expandable device may be used interchangeably herein.

Figure 1:
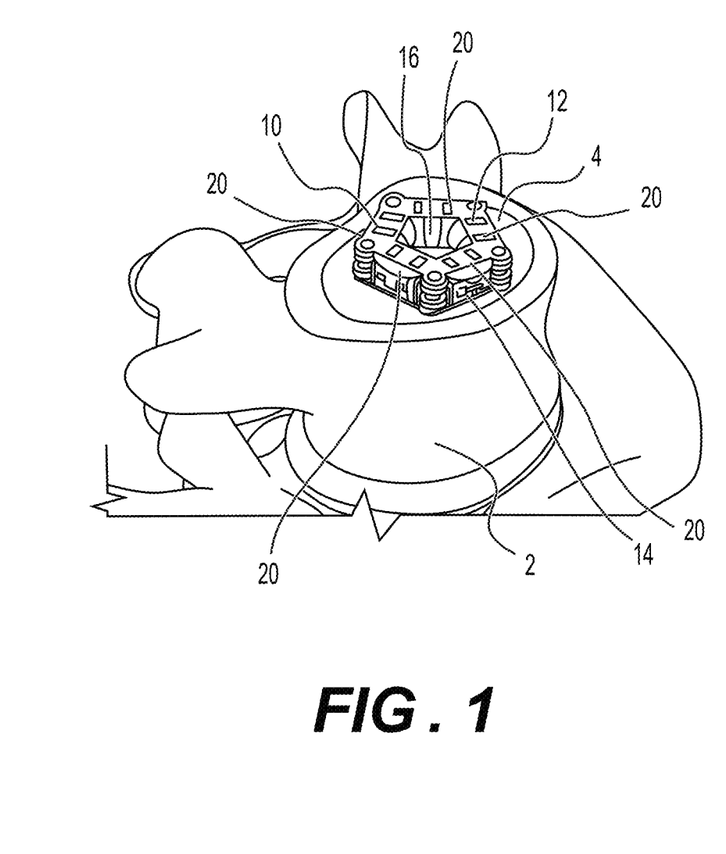
FIG. 1 is a perspective view of an articulating expandable fusion device according to one embodiment, in an articulated collapsed position, shown positioned on a lower vertebra (the upper adjacent vertebra being omitted for clarity)
Figure 2:
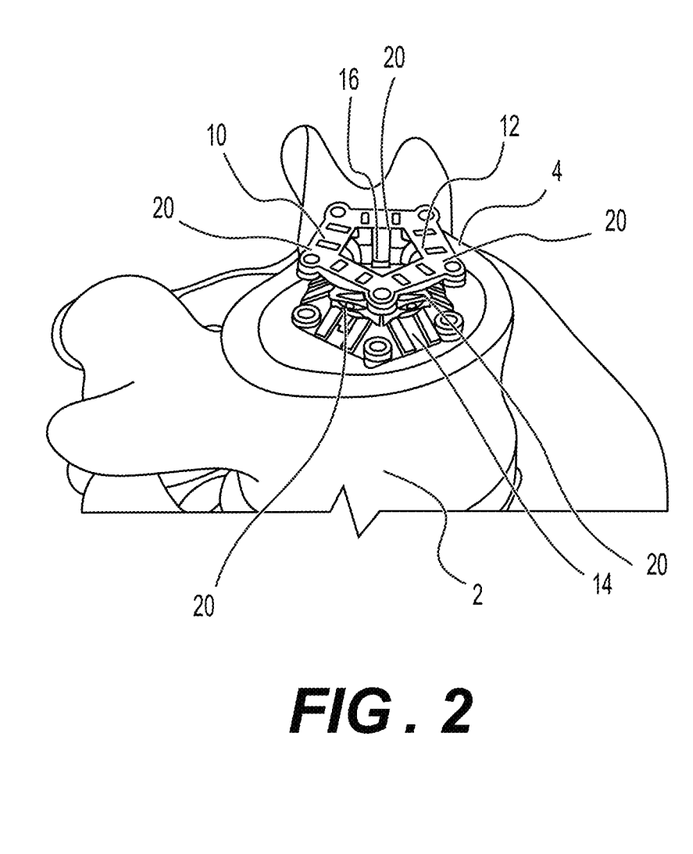
FIG. 2 shows a perspective view of the articulating expandable fusion device of FIG. 1 in an articulated expanded position, shown positioned on the vertebra (the upper adjacent vertebra being omitted for clarity)

Referring now to FIGS. 1 and 2, an articulating expandable fusion device 10 is shown in a disc space between adjacent vertebral bodies 2 (the upper vertebra is omitted for clarity). The fusion device 10 includes a first or upper endplate 12 and a second or lower endplate 14. The upper and lower endplates 12, 14 are configured to engage with the endplates 4 of the adjacent vertebral bodies 2 and, in the installed position, the expanded device 10 is configured to maintain normal intervertebral disc spacing and restore spinal stability, thereby facilitating the intervertebral fusion.

The articulating expandable fusion device 10 may define a central window or opening 16 extending between the upper and lower endplates 12, 14. The central window or opening 16 may be configured to receive bone graft or a similar bone growth inducing material. The bone graft can be introduced within and/or around the fusion device 10 to further promote and facilitate the intervertebral fusion. The fusion device 10, in one embodiment, is preferably packed with bone graft or similar bone growth inducing material to promote the growth of bone through and around the fusion device 10. Such bone graft may be packed between the endplates 4 of the adjacent vertebral bodies 2 prior to, subsequent to, or during implantation of the fusion device 10.

In FIG. 1, the fusion device 10 is shown in an articulated position with the device 10 in a collapsed or contracted position, such that the distance between the upper and lower endplates 12, 14 is provided at a first height. In FIG. 2, the fusion device 10 is shown in an articulated position with the device 10 in an expanded position, such that the distance between the upper and lower endplates 12, 14 is provided at a second height, greater than the first height. The articulating expandable fusion device 10 can be manufactured from a number of biocompatible materials including, but not limited to, titanium, stainless steel, titanium alloys, non-titanium metallic alloys, polymeric materials, plastics, plastic composites, PEEK, ceramic, and elastic materials.

With further emphasis on FIGS. 1-4, the articulating expandable fusion device 10 includes a plurality of individual linking segments or links 20. The plurality of linking segments or links 20 are configured to articulate into a generally polygonal shape. The polygon may be convex, concave, simple, intersecting, or of other suitable type. The shape of the polygon may be dictated by the number of segments or links 20 used to build the implant 10. For example, a device 10 with three links 20 may form a triangle, four links 20 may form a quadrilateral, five links 20 may form a pentagon, six links 20 may form a hexagon, etc. Although the device 10 is shown with five links 20 forming a generally pentagonal shape, it is envisioned that the device 10 may have as few as three segments 20 or as many as desired. The polygon may be equilateral with all links 20 having the same length or the links 20 may be of different lengths. The polygon may be equiangular with all angles between links 20 being equal or may be of different angles and forming irregular shapes.

Figure 3:
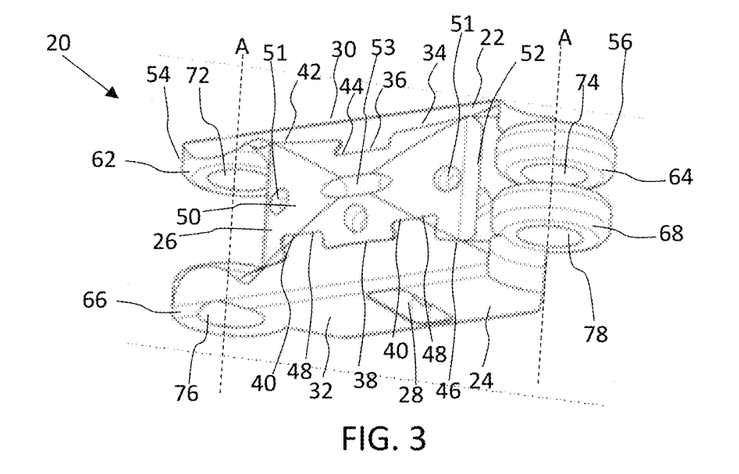
FIG. 3 shows a perspective view of a single link from the articulating expandable fusion device of FIG. 1, with the link in a collapsed position.
Figure 4:
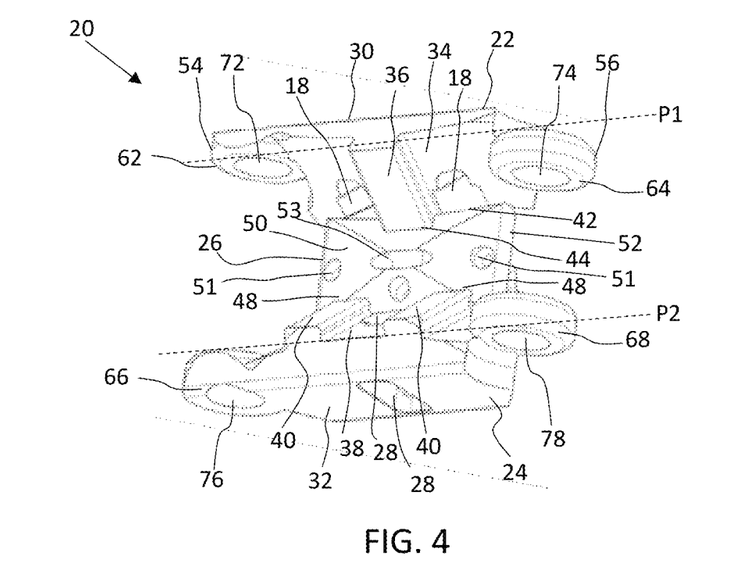
FIG. 4 shows a perspective view of the single link of FIG. 3 with the link in an expanded position.

With further reference to FIGS. 3 and 4, a single link 20 of the device 10 is shown in greater detail. In the embodiment shown, it will be understood that all of the links 20 are identical. It is envisioned, however, that the links 20 may be different from one another. The single link 20 is shown in FIG. 3 in a collapsed or contracted position, and in FIG. 4 in an expanded position. Each link 20 comprises a first body or upper body 22, a second body or lower body 24, and a third inner body or middle body 26 positioned between the upper and lower bodies 22, 24. The upper body 22 includes a bone contacting surface or upper surface 30 which forms a portion of the upper endplate 12 of the device 10 and is configured to engage the endplate 4 of the upper vertebral body 2 (not shown). The lower body 24 includes a bone contacting surface or lower surface 32 which forms a portion of the lower endplate 14 of the device 10 and is configured to engage the endplate 4 of the lower vertebral body 2 (shown in FIGS. 1 and 2).

Figure 5:
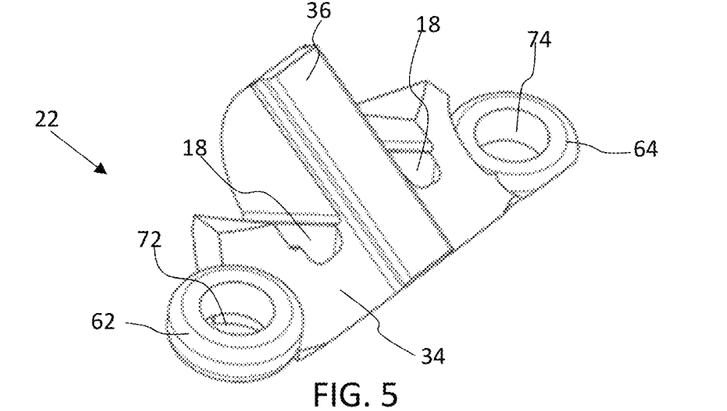
FIG. 5 is a perspective view of the upper body of the link shown in FIGS. 3 and 4.
Figure 7:
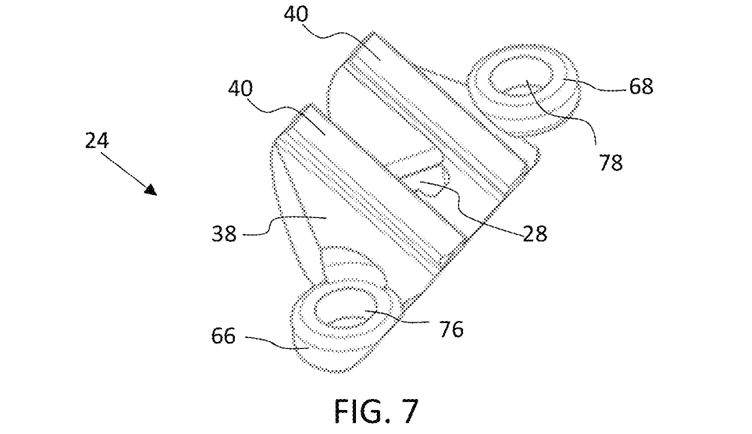
FIG. 7 is a perspective view of the lower body of the link shown in FIGS. 3 and 4.

As best seen in FIG. 5, the upper body 22 includes a lower surface 34 having one or more ramped surfaces 36. The ramped surface 36 may be an angled continuous surface with a given angle of slope. The ramped surface 36 may include male slide ramps or protruding ramps. In the embodiment shown in FIG. 5, a single ramped surface 36 is protruding from the lower surface 34 of the upper body 22. The single ramp 36 may be generally located at the center or midline of the upper body 22. As best seen in FIG. 7, the lower body 24 also includes an upper surface 38 having one or more ramped surfaces 40. The ramped surfaces 38 may be angled continuous surfaces with the same given angle of slope. The ramped surfaces 40 may include male slide ramps or protruding ramps. In the embodiment shown in FIG. 7, two ramped surfaces 40 are protruding from the upper surface 38 of the lower body 24. The two ramped surfaces 40 may be spaced apart at an equal distance such that the ramps 40 are substantially parallel to one another. Although a specific arrangement of ramped surfaces 36, 40 is shown, it is envisioned that the number, location, and configuration of ramped surfaces 36, 40 may be modified or selected by one skilled in the art.

The upper body 22 may include one or more openings 18 extending from the lower surface 34 to the upper surface 30 or recessed through a portion thereof. The openings 18 may be configured to receive a portion of the ramps 40 of the lower body 24, for example, when the links 20 are in the collapsed position. Similarly, the lower body 24 may include one or more openings 28 extending from the upper surface 38 to the lower surface 24 or recessed through a portion thereof. The opening 28 may be configured to receive a portion of the ramp 36 of the upper body 22, for example, when the links 20 are in the collapsed position. In addition, the openings 18, 28 may be configured to receive graft material, if desired.

Figure 6:
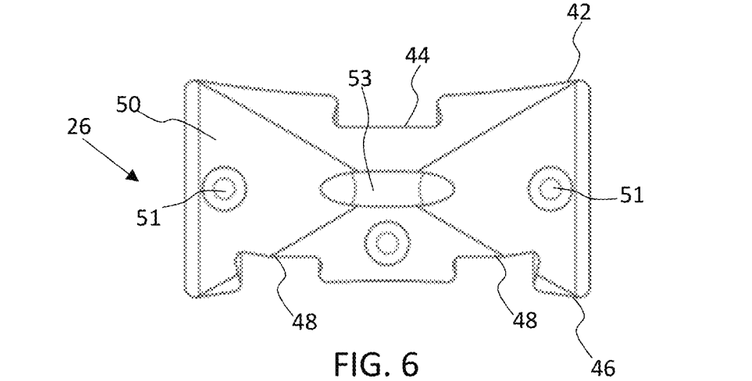
FIG. 6 is a side view of the middle body of the link shown in FIGS. 3 and 4.

The male ramped surfaces 36, 40 are configured to mate with corresponding female ramped surfaces 44, 48 in the middle body 26. The middle body 26 may include an upper surface 42 having one or more female ramped surfaces 44 recessed into the upper surface 42 and a lower surface 46 having one or more female ramped surfaces 48 recessed into the lower surface 46. The protruding male ramped surface 36 of the upper body 22 may be configured to be received within the recessed female ramped surface 44 of the middle body 26 and the protruding male ramped surfaces 40 of the lower body 24 may be configured to be received within the recessed female ramped surfaces 48 of the middle body 26. The ramped surfaces 44, 48 may be angled continuous surfaces with given angles of slope. The angle of slope of the female ramps 44, 48 may match the angle of slope of their respective male ramps 36, 40. Although the ramps 36, 40 are shown as male ramps and the ramps 44, 48 are shown as female ramps, it is envisioned that these ramps could be reversed such that the upper and lower bodies 22, 24 have the female portions and the middle body 26 includes the male portions.

The male ramped surfaces 36, 40 and female ramped surfaces 44, 48 may be configured to mate such that a slidable dovetail joint is formed. For example, a slidable dovetail joint may be formed by one or more tapered projections or tenons (ramps 36, 44) which interlock with corresponding tapered recesses or mortises (ramps 44, 48). The protrusions of the male ramps 36, 40 may be tapered such that they are narrower towards the base and wider towards the mating surfaces of the female ramps 44, 48. Similarly, the recesses of the female ramps 44, 48 may be tapered such that they are narrow towards surfaces 42, 46 and wider toward the mating surfaces of the male ramps 36, 40. The male ramped surface 36, 40 and female ramped surfaces 44, 48 may be substantially linear along their lengths or may be curved, stepped, or otherwise configured to provide for the desired type and amount of expansion between the upper and lower bodies 22, 24.

The inner or middle body 26 includes an outer surface 50 and an inner surface 52. The outer surface 50 is configured to face outwardly when the plurality of links 20 are articulated into the polygonal shape. The inner surface 52 is configured to face inwardly when the plurality of links 20 are articulated into the polygonal shape. The inner surfaces 52 of the links 20 may partially define the central opening 16 of the device 10 when in the expanded position. One or more openings 51, 53 may be provided along or through the outer surface 50 of the middle body 26. For example, a plurality of openings 51 may extend through the outer surface 50 of the middle body 26 and may be configured to receive a wire or cable 76 of an inserter device 70. The face of the outer surface 50 may also define a recess 53. The recess 53 may be elongated having a length greater than its width and configured to receive a portion of the cable 76 of the inserter device 70. The openings 51 and recess 53 may be aligned along a common axis. The recess 53 may be configured to guide the cable 76 between the two openings 51 on either side of the recess 53. Operation of the cable 76 and inserter device 70 will be described in more detail below.

With further emphasis on FIGS. 3 and 4, the expansion mechanism will be further described. In the collapsed or contracted position shown in FIGS. 1 and 3, the middle body 26 is generally positioned towards the perimeter or outer wall of the implant 10 and the upper and lower surfaces 30, 32 are provided at their smallest, initial height. When all of the links 20 are collapsed, the upper and lower endplates 12, 14 of the implant 10 are collapsed (FIG. 1). As an inward force is provided against each of the middle bodies 26, the force translates the middle body 26 inwards toward the center of the polygon, resulting in linear expansion of the upper and lower surfaces 30, 32 of the upper and lower bodies 22, 24.

As shown in the expanded position in FIGS. 2 and 4, the middle body 26 is generally positioned towards the inside or center of the implant 10 and the upper and lower surfaces 30, 32 are provided at their greatest, expanded height. Thus, movement of middle body 26 along the respective ramps 36, 40 of the upper and lower bodies 22, 24 toward the inside or center of the device 10 causes the upper and lower bodies 22, 24 to expand away from one another. When all of the links 20 are expanded, the upper and lower endplates 12, 14 of the implant 10 are expanded (FIG. 2). Similarly, if the middle body 26 was moved along the ramps 36, 40 in the opposite direction toward the outside of the device 10, the upper and lower bodies 22, 24 collapse toward one another, thereby returning to the collapsed position.

Figure 8:
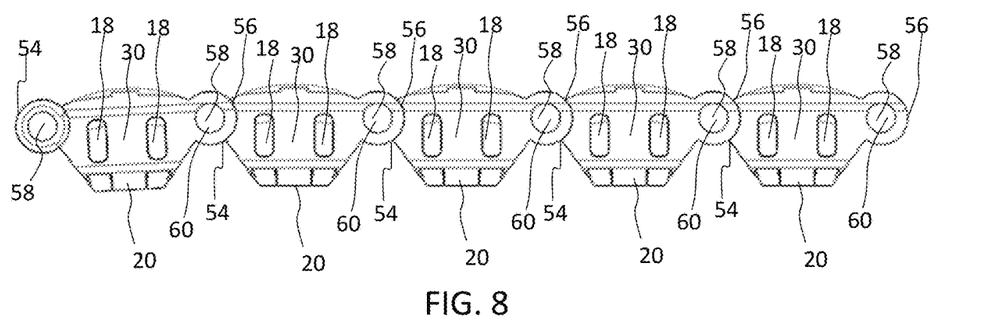
FIG. 8 shows a top view of the articulating expandable fusion device of FIG. 1 with a plurality of links aligned in a substantially straight or non-articulated position.

Turning now to FIG. 8, a plurality of links 20 in a generally linear configuration is shown. Each link 20 extends from a first end 54 to a second end 56. In the embodiment shown, five links 20 are connected such that the second end 56 of a given link 20 connects to the first end 54 of the next link 20 in the chain. For example, the second end 56 of the first link 20 connects to the first end 54 of the second link 20, the second end 56 of the second link 20 connects to the first end 54 of the third link 20, the second end 56 of the third link 20 connects to the first end 54 of the fourth link 20, the second end 56 of the fourth link 20 connects to the first end 54 of the fifth link 20. The linkages would continue if further links 20 were provided. Once articulated into the final polygonal shape, the second end 56 of the fifth link 20 connects to the first end 54 of the first link 20.

Each of the links 20 are connected and able to articulate about a joint 58. The joint 58 may be a revolute joint such as a pin joint or hinge joint. For example, the joint 58 may provide a uni-axial rotation or single-axis rotation about one or more pins 60, for example. The connected links 20 may be able to rotate freely about the axis A of each respective pin 60 between connected links 20. Although pins 60 are exemplified herein, it will be appreciated that other joint geometries may be used.

In one embodiment, the joints 58 may include a plurality of retaining rings 62, 64, 66, 68. As best seen in FIGS. 3 and 4, each upper body 22 may include first and second upper retaining rings 62, 64, and each lower body 24 may include first and second lower retaining rings 66, 68. For example, the upper body 22 may include first upper retaining ring 62 at the first end 54 and second upper retaining ring 64 at the second end 56 of the link 20. The lower body 24 may include first lower retaining ring 66 at the first end 54 and second lower retaining ring 68 at the second end 56 of the link 20. The first upper retaining ring 62 may be generally aligned with the first lower retaining ring 66 and the second upper retaining ring 64 may be generally aligned with the second lower retaining ring 68. The retaining rings 62, 64, 66, 68 may define a generally circular or rounded outer body or may be otherwise configured to provide movement of the joints 58. The retaining rings 62, 64, 66, 68 may define cylinders, tubes, polyhedrons, prisms, or other suitable shapes.

As best seen in FIG. 4, the first rings 62, 66 may be generally offset relative to the second rings 64, 68. For example, the first upper ring 62 may be generally positioned above a first plane P1 whereas the second upper ring 64 may be generally positioned below the first plane P1. The first lower ring 66 may be generally positioned below a second plane P2 and the second lower ring 68 may be generally positioned above the second plane P2. In this configuration, regardless of the amount of expansion, the distance between the first upper ring 62 and the first lower ring 66 is greater than the distance between the second upper ring 64 and the second lower ring 68. In addition, in the embodiment shown, the first upper retaining ring 62 may have at least a portion of its upper surface generally aligned with the bone contacting surface 30 of the upper body 22 and the first lower retaining ring 66 may have at least a portion of its lower surface generally aligned with the bone contacting surface 32 of the lower body 24. Although the offsets are shown in a given configuration, it will be appreciated that the number, location, and type of retaining rings may be modified.

The retaining rings 62, 64, 66, 68 define respective openings 72, 74, 76, 78 extending therethrough configured to receive one or more pivot pins 60. For example, ring 62 may include a central opening 72 extending from an upper surface to a lower surface of the ring 62. Ring 64 may include a central opening 74 extending from an upper surface to a lower surface of the ring 64. Ring 76 may include a central opening 76 extending from an upper surface to a lower surface of the ring 66. Ring 68 may include a central opening 78 extending from an upper surface to a lower surface of ring 68. Openings 72 and 76 may be generally aligned and openings 74 and 78 may be generally aligned with one another.

By way of example, mating of the retaining rings 62, 64, 66, 68 between links 20 will be described with respect to a series of three links 20. Although it will be appreciated that such connections (including additional retaining rings 62, 64, 66, 68 and pivot pins 60) may continue in series when additional links 20 are present. The second upper retaining ring 64 of the first link 20 connects to the first upper retaining ring 62 of the second link 20 with a first pivot pin 60. The second lower retaining ring 68 of the first link 20 connects to the first lower retaining ring 66 of the second link 20 with a second pivot pin 60. The second upper retaining ring 64 of the second link 20 connects to the first upper retaining ring 62 of the third link 22 with a third pivot pin 60. The second lower retaining ring 68 of the second link 20 connects to the first lower retaining ring 66 of the third link 20 with a fourth pivot pin 60.

FIG. 8 depicts the plurality of links 20 in a generally linear configuration suitable for being guided through an inserter instrument 70. FIGS. 9-12 depicts deployment of the links 20 through the inserter instrument 70 in a collapsed position.

Figure 9:
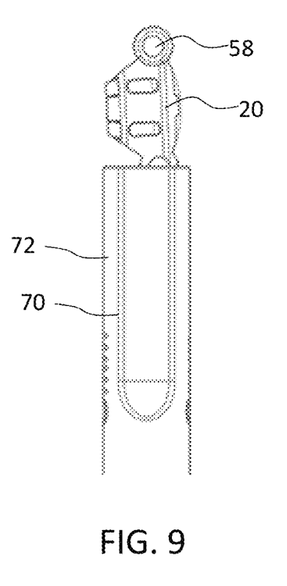
FIG. 9 shows a top view of the articulating expandable fusion device of FIG. 1 with a first link deployed through an inserter instrument according to one embodiment.
Figure 10:
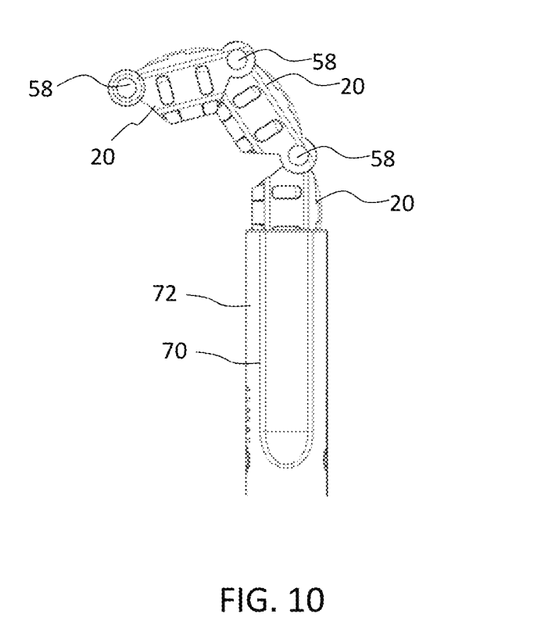
FIG. 10 shows a top view of the articulating expandable fusion device of FIG. 1 with a plurality of links deployed through the inserter instrument and beginning to articulate.
Figure 11:
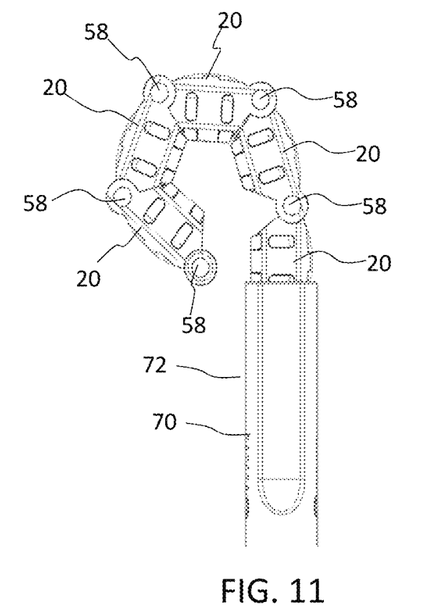
FIG. 11 shows a top view of the articulating expandable fusion device of FIG. 1 with a plurality of links deployed through the inserter instrument and almost fully articulated into a polygonal shape.
Figure 12:
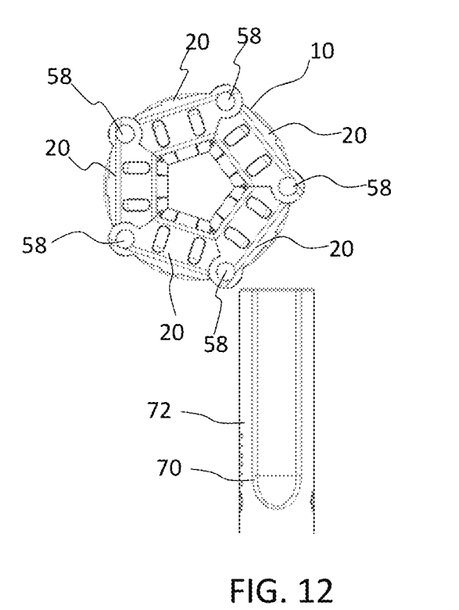
FIG. 12 is a top view of the articulating expandable fusion device of FIG. 1 completely deployed from the inserter instrument and fully articulated in a collapsed position.

The inserter instrument 70 may include a cannula or guide tube 72 that the links 20 can pass through. The guide tube 72 may be suitable for use during a minimally invasive surgical (MIS) procedure, for example. As shown in FIG. 9, a first link 20 is deployed through the inserter instrument 70 in a collapsed position. In FIG. 10, additional links 20 are deployed through the inserter instrument 70 and the links 20 are beginning to articulate. In FIG. 11, most of the links 20 are deployed through the inserter instrument 20 and the links 20 are almost fully articulated into its polygonal shape (a pentagon in this case). In FIG. 12, the implant 10 is completely deployed from the inserter instrument 70 and all of the links 20 are fully articulated into a polygon in the collapsed position.

Figure 13:
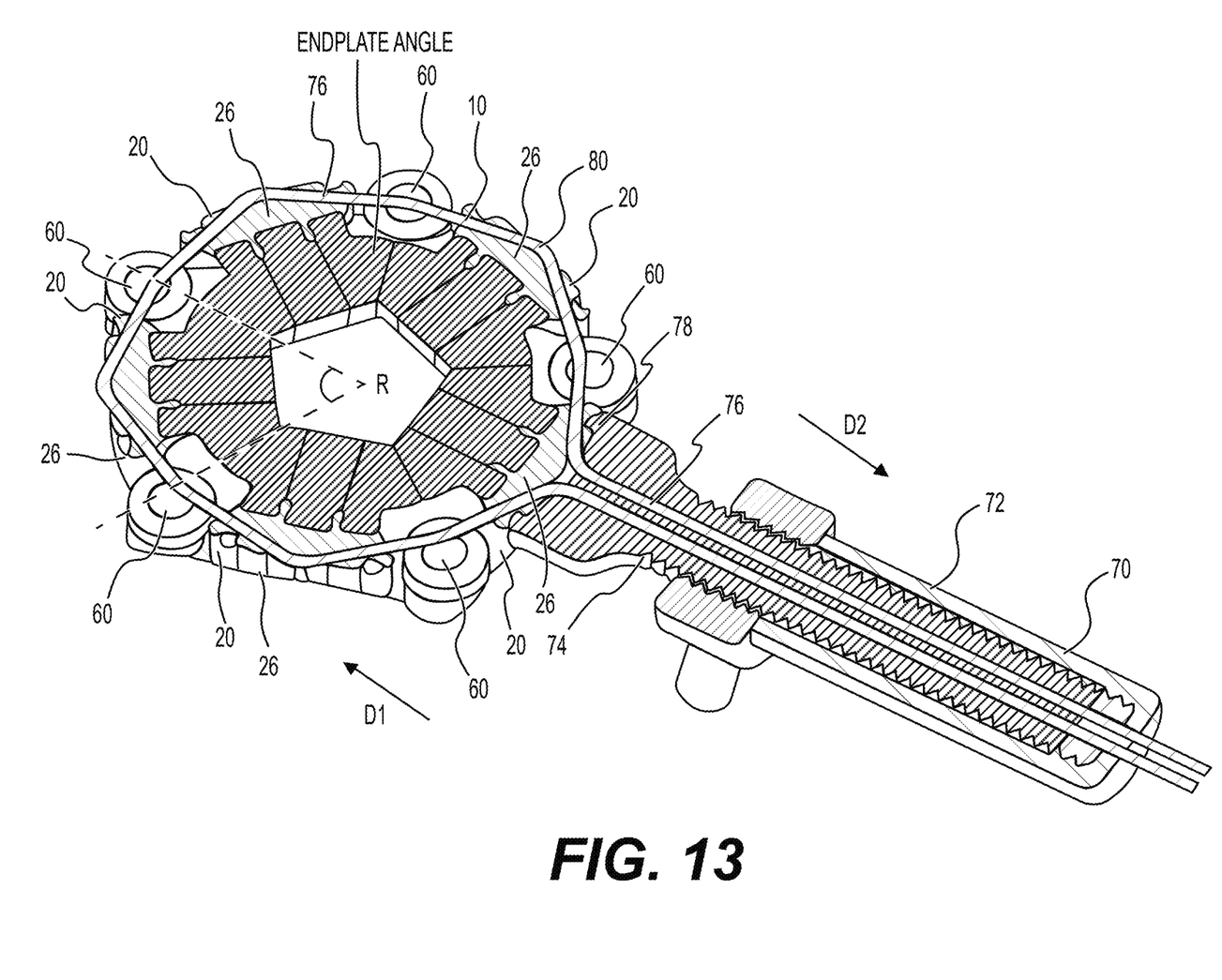
FIG. 13 is a cross-sectional view of the articulating expandable fusion device in the collapsed position and an instrument configured for expanding the fusion device.

Although five links 20 are depicted in this embodiment to form a pentagon, it will be appreciated that a suitable number of links 20 may be selected. As best seen in FIG. 13, a reference angle R of the endplates of the assembled links 20 is dictated by the number of links 20 used to build the implant 10. For example, the reference angle R for a triangle is 120 degrees, reference angle R for a square is 90 degrees, reference angle R for a pentagon is 72 degrees, reference angle R for a hexagon is 60 degrees, etc.

Figure 14:
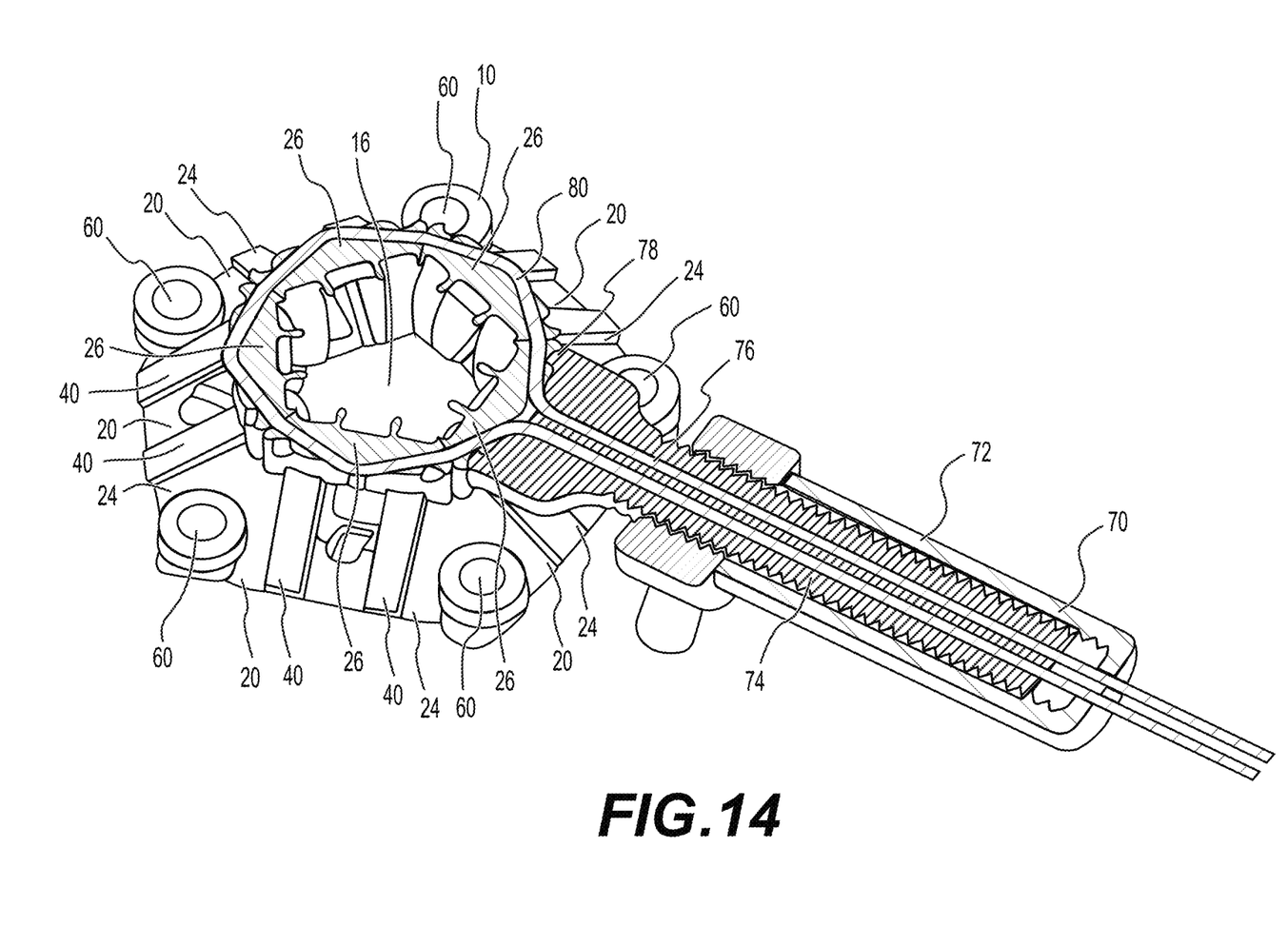
FIG. 14 is a cross-sectional view of the articulating expandable fusion device in an expanded position and the instrument expanding the fusion device.

With further emphasis on FIGS. 13 and 14, the inserter instrument 70 may include guide tube 72, an insertion driver 74 positionable through the guide tube 72, and a wire or cable 76 positionable through the insertion driver 74. As noted with regard to FIGS. 9-12, the guide tube 72 may be configured for deploying the plurality of links 20 into the disc space. The insertion driver 74 and cable 76 may be configured for articulating the plurality of links 20 into a polygon. The cable 76 may be further configured for applying an inward force against the middle bodies 26 of the links 20 to translate the middle bodies 26 towards a center of the polygon to cause linear expansion of the upper and lower bodies 22, 24 of the links 20.

The distal end 78 of the insertion driver 74 may retain the implant 10 to the inserter instrument 70. For example, the distal end 78 of the insertion driver 74 may include one or more engagement features configured for mating with the implant 10. In particular, the distal end 78 of the insertion driver 74 may be configured to mate with one of the middle bodies 26 of one of the links 20. The insertion driver 74 extends through the guide tube 72 and may be threaded to a portion of the guide tube 72 or otherwise engaged thereto.

The wire or cable 76 extends through the insertion driver 74 and is configured to loop 80 around the links 20. In particular, the cable 76 may interface with the middle bodies 26 of the links 20. The cable 76 may extend through one or more openings 51, 53 in the middle bodies 26 of the links 20. In order to articulate the implant 10, a push/pull action may be used. For example, the insertion driver 74 may push the links 20 in the direction D1 while the cable 76 pulls the links 20 in the direction D2, opposite to D1. Although this push/pull articulation is exemplified, it will be appreciated that other articulation methods may be used, such as via one or more cam members, guiding members, or the like.

The wire or cable 76 may loop 80 about the outer perimeter of the links 20. As best seen in FIG. 13, the implant 10 is in the collapsed or contracted position and the cable 76 is looped 80 around and through the middle bodies 26 of the links 20. Turning to FIG. 14, the implant 10 is in the expanded position. To expand the implant 10, the cable 76 may shorten in circumferential distance to provide an inward force that translates the middle bodies 26 inwards toward the center of the polygon. The inward movement of the middle bodies 26 of the links 20 may result in linear expansion of the upper and lower bodies 22, 24 of each of the links 20.

In the collapsed position (FIG. 13), the loop 80 of the cable 76 has a first length and in the expanded position (FIG. 14), the loop 80 of the cable 76 has a second length, shorter than the first length. By applying an inward force against the middle bodies 26 of the links 20, the articulated implant 10 is further expanded such that the distance between the upper and lower endplates 12, 14 is at its greatest height. Although expansion with cable 76 is exemplified herein, it will be appreciated that other mechanisms may be utilized to move the middle bodies 26, such as translation members, linear cams, drive screws, or other suitable devices.

In order to improve the access profile of the interbody implant 10 while maximizing cortical bone contact surface area, methods and systems of installing, articulating, and/or expanding the implant 10 may include one or more of the following. The implant 10 may enter the disc space with a narrow profile and articulate to increase surface area contact on the anterior apophyseal ring. The orientation and position of the interbody implant 10 in its final implanted position may be optimized by pre-/intra-op scans and/or normal population statistics that determine bone mineral density maps of the vertebral body. Robotic and/or navigation guidance may be used to correctly orient the interbody 10. Further details of robotic and/or navigational systems can be found in U.S. Patent Publication No. 2017/0239007, which is incorporated herein by reference in its entirety for all purposes.

In one embodiment, the system may be implanted with one or more of the following steps: (1) A determination is made on final optimal implant location to optimize bone mineral density of the contacted bone/implant interface. (2) Robotic and/or navigation is used to determine the potential trajectories that will allow for this optimal implant location to be achieved. (3) A cannula is docked on the disc space through Kambin's triangle, or the anatomical area that is bordered by the disc space, exiting nerve root, and traversing nerve root. (4) The expandable interbody 10 is inserted in the non-articulated, non-expanded orientation. (5) The expandable interbody 10 is impacted for insertion, and the wire or cable 76 is pulled for articulation. (6) The expandable interbody 10 articulates to a polygonal shape that precisely matches the native disc space anatomy. (7) The expandable interbody 10 expands by shortening the cable 76 about the middle bodies 26 of the links 20 and translating them inwards toward a center of the polygonal shape.

The features of the embodiments described herein may provide one or more of the following advantages. A small insertion profile such as an 8.5 mm lateral insertion profile and minimal insertion height into the disc space may reduce skin, fascia, muscle, and/or ligamentous disruption. The large endplate surface area contact may help to reduce the risk of subsidence, or migration of the implant through the bone endplates of the inferior and superior interbody, especially during expansion. Due to the expansion profile of the implant, reduced endplate disruption may result. The expansion mechanism may reduce the need for traditional trialing of interbody implants which may contribute to endplate disruption. It will be appreciated that different or additional advantages may also be achieved based on the disclosure herein.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:
a cable defining a longitudinal axis;
an upper body;
a lower body; and
a core body slidably disposed between the upper and lower bodies, and including a plurality of links each adapted to be arranged in series with each other inside an insertion device with a first one of the links disposed at a distal end and a last one of the links disposed at a proximal end, the cable being routed through each of the links in series such that when one end of the cable is pulled, one end of the first link moves proximally towards one end of the last link, the core body slidable relative to at least one of the upper and lower bodies to expand the upper body relative to the lower body, wherein the core body is slidable in a direction perpendicular to the longitudinal axis of the cable.

2. The expandable implant of claim 1, wherein the plurality of links are configured to articulate into a polygonal shape.

3. The expandable implant of claim 1, wherein the plurality of links includes five links configured to articulate into a pentagon.

4. The expandable implant of claim 1, wherein each of the links includes a through hole through which the cable is routed.

5. The expandable implant of claim 1, wherein:
the upper body includes a plurality of pivotally connected segments;
the lower body includes a plurality of pivotally connected segments, the core body positioned between and slidably coupled to at least one of the upper and lower bodies.

6. The expandable implant of claim 5, wherein the upper body includes one or more ramped surfaces, the lower body includes one or more ramped surfaces, and the core body includes one or more ramped surfaces, wherein translation of the core body causes the ramped surfaces of the core body to slide against the ramped surfaces of the upper and lower bodies, thereby resulting in vertical expansion of the expandable implant.

7. The expandable implant of claim 6, wherein the ramped surfaces of the upper and lower bodies, respectively, define male ramps, and the ramped surfaces of the core body define female ramps.

8. The expandable implant of claim 7, wherein the male ramps of the upper and lower bodies mate with the female ramps of the core body with dovetail slide ramps.

9. The expandable implant of claim 6, wherein the upper body mates with the core body at a single ramp, and the lower body mates with the core body at two ramps.

10. The expandable implant of claim 6, wherein each of the upper bodies includes first and second upper retaining rings, and each of the lower bodies includes first and second lower retaining rings, wherein the second upper retaining ring of the first segment connects to the first upper retaining ring of the second segment with a first pivot pin, the second lower retaining ring of the first segment connects to the first lower retaining ring of the second segment with a second pivot pin, the second upper retaining ring of the second segment connects to the first upper retaining ring of the third segment with a third pivot pin, and the second lower retaining ring of the second segment connects to the first lower retaining ring of the third segment with a fourth pivot pin.

11. An implantable device comprising:
a cable defining a longitudinal axis;
an upper body adapted to be in contact with a lower surface of a vertebral body;
a lower body adapted to be in contact with an upper surface of another vertebral body;
a core body slidably interposed between the upper and lower bodies, the core body including a plurality of links each adapted to be arranged in series with each other inside an insertion device with a first one of the links disposed at a distal end and a last one of the links disposed at a proximal end, the cable being routed through each of the links in series such that when one end of the cable is pulled, one end of the first link moves proximally towards one end of the last link and expand the upper body relative to the lower body by sliding the core body relative to the upper body to the lower body in a direction perpendicular to the longitudinal axis.

12. The implantable device of claim 11, wherein:
the upper body includes a plurality of pivotally connected segments coupled to the corresponding ones of the core body links,
the lower body includes a plurality of pivotally connected segments coupled to the corresponding ones of the core body links.

13. The expandable implant of claim 12, wherein the plurality of links and the corresponding segments of the upper and lower bodies are configured to articulate into a polygonal shape.

14. The expandable implant of claim 13, wherein the plurality of links includes five links configured to articulate into a pentagon.

15. The expandable implant of claim 12, wherein the core body is slidably coupled to the upper and lower bodies.

16. The expandable implant of claim 12, wherein the upper body includes a plurality of ramped surfaces and the core body includes one or more ramped surfaces, wherein translation of the core body causes the ramped surfaces of the core body to slide against the ramped surfaces of the upper body, thereby causing vertical expansion of the expandable implant.

17. The expandable implant of claim 12, wherein the lower body includes a plurality of ramped surfaces and the core body includes ramped surfaces, wherein translation of the core body causes the ramped surfaces of the core body to slide against the ramped surfaces of the lower body, thereby causing vertical expansion of the expandable implant.

18. The expandable implant of claim 11, wherein each of the links includes a through hole through which the cable is routed.

19. The expandable implant of claim 11, wherein:
the upper body includes a plurality of pivotally connected segments coupled to the corresponding ones of the core body links;
the lower body includes a plurality of pivotally connected segments coupled to the corresponding ones of the core body links; and
the core body is slidably coupled to the upper and lower bodies.

20. The expandable implant of claim 19, wherein each of the core body links is slidably coupled to a corresponding one of the upper body segments.

* * * * *